(12) United States Patent
Morisaki (10) Patent No.: US 11,179,176 B2
(45) Date of Patent: Nov. 23, 2021

(54) GRASPING TREATMENT INSTRUMENT AND MANUFACTURING METHOD OF GRASPING TREATMENT INSTRUMENT

(71) Applicant: OLYMPUS CORPORATION, Hachioji (JP)

(72) Inventor: Kazuhiro Morisaki, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 152 days.

(21) Appl. No.: 16/242,407

(22) Filed: Jan. 8, 2019

(65) Prior Publication Data

US 2019/0133636 A1     May 9, 2019

Related U.S. Application Data

(60) Provisional application No. PCT/JP2016/070718, filed on Jul. 13, 2016.

(51) Int. Cl.
| | | |
|---|---|---|
| *A61B 17/32* | (2006.01) | |
| *A61B 17/28* | (2006.01) | |
| *A61B 17/295* | (2006.01) | |

(52) U.S. Cl.
CPC .... *A61B 17/320092* (2013.01); *A61B 17/282* (2013.01); *A61B 17/295* (2013.01); *A61B 17/32* (2013.01); *A61B 2017/320072* (2013.01)

(58) Field of Classification Search
CPC ..... A61B 17/32; A61B 17/282; A61B 17/295; A61B 17/320092; A61B 2017/320095
See application file for complete search history.

(56) References Cited

U.S. PATENT DOCUMENTS

| | | |
|---|---|---|
| 6,024,750 A | 2/2000 | Mastri et al. |
| 6,432,118 B1 | 8/2002 | Messerly |
| 6,468,286 B2 | 10/2002 | Mastri et al. |
| 6,682,544 B2 | 1/2004 | Mastri et al. |

(Continued)

FOREIGN PATENT DOCUMENTS

| | | |
|---|---|---|
| JP | 2003-527155 A | 9/2003 |
| WO | 2011/099571 A1 | 8/2011 |
| WO | 2016/006379 A1 | 1/2016 |

OTHER PUBLICATIONS

Jan. 15, 2019 Preliminary Report on Patentability issued in International Patent Application No. PCT/JP2016/070718.

(Continued)

*Primary Examiner* — Tuan V Nguyen
(74) *Attorney, Agent, or Firm* — Oliff PLC (57) ABSTRACT

A grasping treatment instrument includes a holder openable and closable relative to a treatment section. A pad extends straight in a natural state, and is attached along an installation surface of the holder. A holder inclined surface is provided on the installation surface, and inclines in a state that the holder inclined surface extends toward a treatment section side as extending toward a distal side. A pad inclined surface is formed in the pad attached to the holder, and is formed in a state that the pad inclined surface is elastically deformed along an inclination of the holder inclined surface. The pad inclined surface inclines in a state that the pad inclined surface extends toward the treatment section side as extending toward the distal side.

11 Claims, 7 Drawing Sheets

(56) References Cited

U.S. PATENT DOCUMENTS

| | | | |
|---|---|---|---|
| 2001/0025184 A1* | 9/2001 | Messerly | A61B 17/320092 |
| | | | 606/169 |
| 2002/0019646 A1 | 2/2002 | Mastri et al. | |
| 2003/0009186 A1 | 1/2003 | Mastri et al. | |
| 2004/0147946 A1 | 7/2004 | Mastri et al. | |
| 2006/0122639 A1 | 6/2006 | Mastri et al. | |
| 2009/0030440 A1 | 1/2009 | Mastri et al. | |
| 2009/0270853 A1* | 10/2009 | Yachi | A61B 17/320092 |
| | | | 606/27 |
| 2011/0166483 A1 | 7/2011 | Mastri et al. | |
| 2012/0179182 A1 | 7/2012 | Mastri et al. | |
| 2013/0245658 A1 | 9/2013 | Mastri et al. | |
| 2015/0164532 A1 | 6/2015 | Faller et al. | |

OTHER PUBLICATIONS

Nov. 5, 2019, Office Action issued in Japanese Patent Application No. 2018-527313.
Sep. 20, 2016 International Search Report issued in International Patent Application No. PCT/JP2016/070718.
Oct. 28, 2020 Office Action issued in Chinese Patent Application No. 201680087563.6.

* cited by examiner

GRASPING TREATMENT INSTRUMENT AND MANUFACTURING METHOD OF GRASPING TREATMENT INSTRUMENT

CROSS-REFERENCE TO RELATED APPLICATIONS

This is a Continuation Application of PCT Application No. PCT/JP2016/070718, filed Jul. 13, 2016, the entire contents of which are incorporated herein by reference.

BACKGROUND OF THE INVENTION

1. Field of the Invention

The present invention relates to a grasping treatment instrument which grasps a treatment target between a treatment section, which is provided in a distal portion of a rod member, and a grasping piece. Further, the present invention relates to a manufacturing method of this grasping treatment instrument.

2. Description of the Related Art

WO2011/099571A1 discloses a grasping treatment instrument including a rod member which can transmit ultrasonic vibration. In this grasping treatment instrument, a treatment section is provided in a distal portion of the rod member, and a grasping piece is openable and closable relative to the treatment section. The treatment section includes a treatment surface which faces the grasping piece, and the grasping piece includes a pad member. In a state in which the grasping piece is closed relative to the treatment section, an abutment surface of the pad member is abuttable on the treatment surface of the treatment section. A distal portion of the treatment surface is provided with a treatment section inclined surface which inclines in a state that the treatment section inclined surface extends toward a back surface side of the treatment section as extending toward a distal side. In addition, a distal portion of the abutment surface includes a pad inclined surface which inclines in a state that the pad inclined surface extends toward the treatment section side as extending toward the distal side. In a state in which the abutment surface of the pad member abuts on the treatment surface of the treatment section, the pad inclined surface abuts on the treatment section inclined surface. By providing the treatment section inclined surface and the pad inclined surface, a treatment target, such as a biological tissue, which is grasped between the grasping piece and treatment section, is effectively prevented from slipping down toward the distal side.

BRIEF SUMMARY OF THE INVENTION

According to one aspect of the invention, a grasping treatment instrument includes that: a rod extending along a longitudinal axis, the rod being configured to transmit ultrasonic vibration from a proximal side to a distal side; a treatment section including a treatment surface, the treatment section being provided in a distal portion of the rod; a holder openable and closable relative to the treatment section, the holder including an installation surface which faces a treatment section side; a pad extending straight in a natural state, the pad being attached along the installation surface of the holder, and the pad including an abutment surface which is abuttable on the treatment surface; a holder inclined surface provided on a distal portion of the installation surface in the holder, the holder inclined surface inclining in a state that the holder inclined surface extends toward the treatment section side as extending toward the distal side; and a pad inclined surface formed on a distal portion in the pad attached to the holder, the pad inclined surface being formed in a state in which the pad inclined surface is elastically deformed along an inclination of the holder inclined surface, and the pad inclined surface inclining in a state that the pad inclined surface extends toward the treatment section side as extending toward the distal side.

According to one another aspect of the invention, a manufacturing method of a grasping treatment instrument in which a holder is openable and closable relative to a treatment section, the treatment section being configured to perform a treatment by ultrasonic vibration, the method including: engaging a pad engagement of a pad with a holder engagement of the holder, and moving the pad relative to the holder from a proximal side toward a distal side in a state that the pad engagement is engaged with the holder engagement, the pad being straight in a natural state; elastically deforming the pad along a holder inclined surface, and thereby forming a pad inclined surface, the holder inclined surface being provided on a distal portion of the holder, the pad inclined surface inclining in a state that the pad inclined surface extends toward a treatment section side as extending toward the distal side; and restricting movement of the pad relative to the holder.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

First Embodiment

Figure 1:
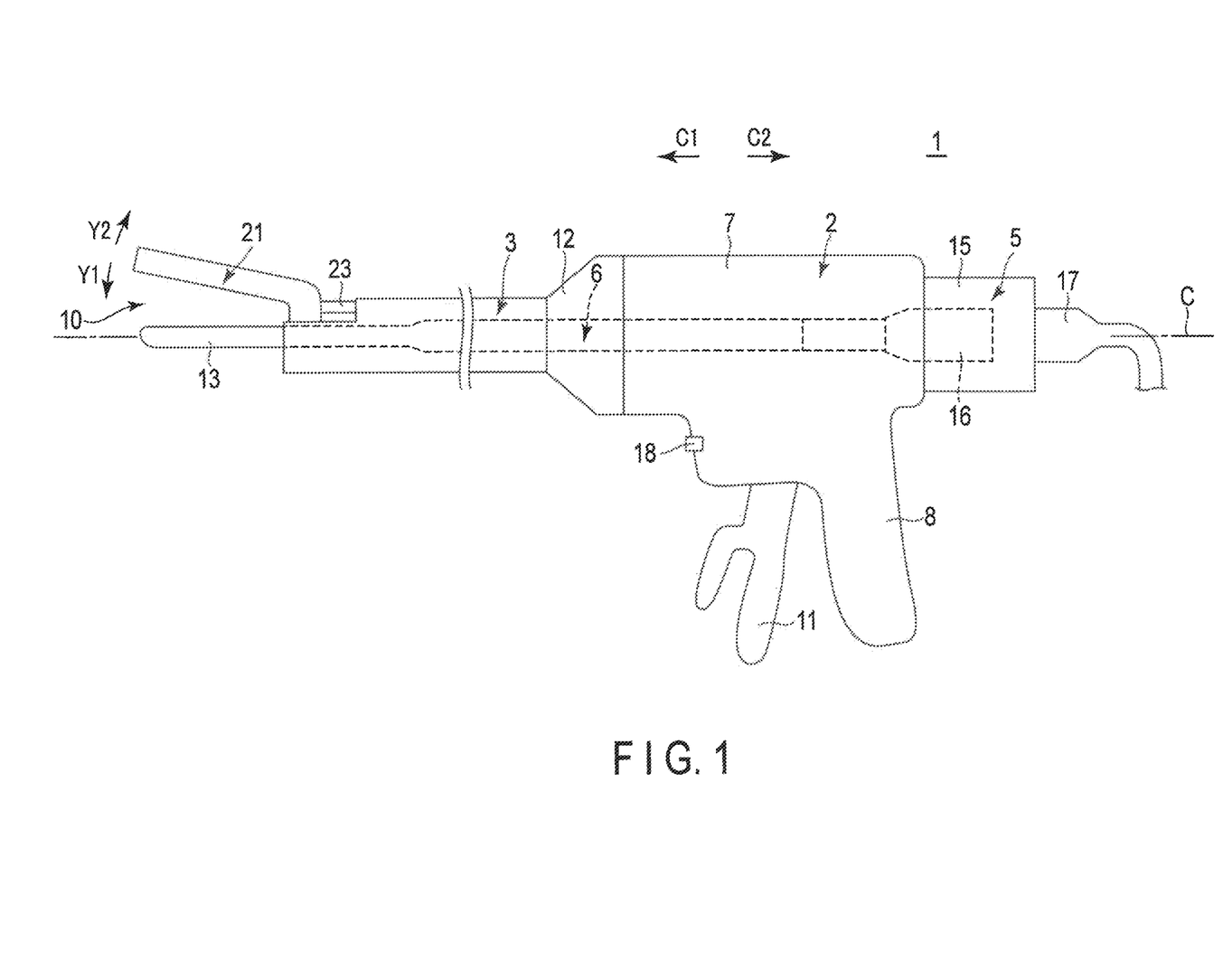
FIG. 1 is a schematic view illustrating a grasping treatment instrument according to a first embodiment.

A first embodiment of the present invention will be described with reference to FIG. 1 to FIG. 14. FIG. 1 is a view illustrating a grasping treatment instrument 1 according to the first embodiment. As illustrated in FIG. 1, the grasping treatment instrument 1 includes a housing 2, a shaft 3, a transducer unit 5, and a rod member (rod) 6. The shaft 3 has a longitudinal axis C as a center axis. Here, one side in a direction along the longitudinal axis C is a distal side (arrow C1 side), and a side opposite to the distal side is a proximal side (arrow C2 side). The shaft 3 extends along the longitudinal axis C.

The housing 2 is holdable, and is coupled to the proximal side of the shaft 3. The housing 2 includes a housing body 7 which extends along the longitudinal axis C, and a grip 8 which extends from the housing body 7 in a direction crossing the longitudinal axis C. In addition, a handle 11 is rotatably attached to the housing 2. By the handle 11 rotating relative to the housing 2 around an attachment position to the housing 2, the handle 11 opens or closes relative to the grip 8. In the present embodiment, the handle 11 is located on the distal side with respect to the grip 8, and the direction of movement of the handle 11 relative to the grip 8 in the opening motion and closing motion is substantially parallel to the longitudinal axis C, but this is not restrictive. In one example, the handle 11 may be provided on the proximal side with respect to the grip 8. In another example, the handle 11 and grip 8 may be provided on mutually opposite sides with respect to the longitudinal axis C as the center, and the direction of movement of the handle 11 relative to the grip 8 in the opening motion and closing motion may be substantially perpendicular to the longitudinal axis C.

Besides, in the present embodiment, a rotary member (rotary knob) 12 is attached to the housing body 7 from the distal side. The shaft 3 is inserted into the inside of the rotary member 12 from the distal side. The shaft 3 is fixed to the rotary member 12, and is rotatable together with the rotary member 12 around the longitudinal axis C relative to the housing 2.

The rod member (probe) 6 can transmit ultrasonic vibration, and extends from the inside of the housing 2 toward the distal side along the longitudinal axis C through the inside of the shaft 3. A distal portion of the rod member 6 is provided with a treatment section (rod treatment section) 13. The rod member 6 is inserted through the shaft 3 in such a state that the treatment section (rod-side grasping piece) 13 projects from the distal end of the shaft 3 toward the distal side.

The transducer unit 5 includes a transducer case 15 and an ultrasonic transducer 16. The transducer case 15 is attached to the housing body 7 from the proximal side. In addition, one end of a cable 17 is connected to the transducer case 15. The other end of the cable 17 is detachably connected to an energy control device (not shown). The ultrasonic transducer 16 is disposed in the inside of the transducer case 15. The ultrasonic transducer 16 extends along the longitudinal axis C, and, in the inside of the housing body 7, the ultrasonic transducer 16 is connected to the rod member 6 from the proximal side. Incidentally, in one example, one end of the cable 17 may be connected to the housing 2.

An operation button 18 is attached to the housing 2. An operation for outputting electric energy from the energy control device is input by the operation button 18. If the operation is input by the operation button 18, AC electric power of a predetermined frequency, for instance, is supplied as electric energy from the energy control device to the ultrasonic transducer 16 via electric wiring (not shown) which extends in the inside of the cable 17. Thereby, in the ultrasonic transducer 16 including a piezoelectric element (not shown), the electric energy is converted to ultrasonic vibration, and the ultrasonic vibration is generated. The ultrasonic vibration generated by the ultrasonic transducer 16 is transmitted in the rod member 6 from the proximal side to distal side. Further, the ultrasonic vibration is transmitted to the treatment section 13 of the rod member 6. The ultrasonic transducer 16 and rod member 6 vibrate at a certain frequency in a predetermined frequency range by transmitting the ultrasonic vibration. At this time, the direction of vibration of the rod member 6 and ultrasonic transducer 16 is substantially parallel to the longitudinal axis C. Incidentally, a footswitch or the like, which is separate from the grasping treatment instrument 1, may be provided in place of the operation button 18, or in addition to the operation button 18.

A grasping piece (jaw-side grasping piece) 21 is rotatably attached to a distal portion of the shaft 3. A movable member 23 extends along the longitudinal axis C in the inside of the shaft 3. A distal portion of the movable member 23 is connected to the grasping piece 21. The movable member 23 extends toward the proximal side up to the inside of the housing 2. In the inside of the housing body 7, the handle 11 is coupled to the movable member 23. By the handle 11 opening or closing relative to the grip 8, the movable member 23 moves along the longitudinal shaft C. By the movement of the movable member 23, driving force from the movable member 23 acts on the grasping piece 21, and the grasping piece 21 rotates around an attachment position to the shaft 3. Thereby, the grasping piece 21 opens or closes relative to the treatment section 13. By the grasping piece 21 and treatment section 13 closing relative to each other, a treatment target, such as a biological tissue, can be grasped between the grasping piece 21 and treatment section 13. The closing direction (the direction of arrow Y1) and the opening direction (the direction of arrow Y2) of the grasping piece 21 cross the longitudinal axis C. In addition, in the state in which the grasping piece 21 and treatment section 13 are closed relative to each other, the longitudinal direction of the grasping piece 21 becomes substantially parallel to the longitudinal axis C of the shaft 3. Further, in one example, the movable member 23 may extend on the outside of the shaft 3. In this case, the shaft 3 extends in the inside of the movable member 23.

In the present embodiment, an end effector 10 is formed by the treatment section 13 and grasping piece 21 and, in the end effector 10, the grasping piece 21 is openable and closable relative to the treatment section 13. In addition, the end effector 10 and rod member 6 can rotate together with the shaft 3 and rotary member 12 around the longitudinal axis C, relative to the housing 2. Incidentally, in one example, the rotary member 12 may not be provided, and the shaft 3, end effector 10 and rod member 6 may be configured to be unrotatable around the longitudinal axis C, relative to the housing 2.

Figure 2:
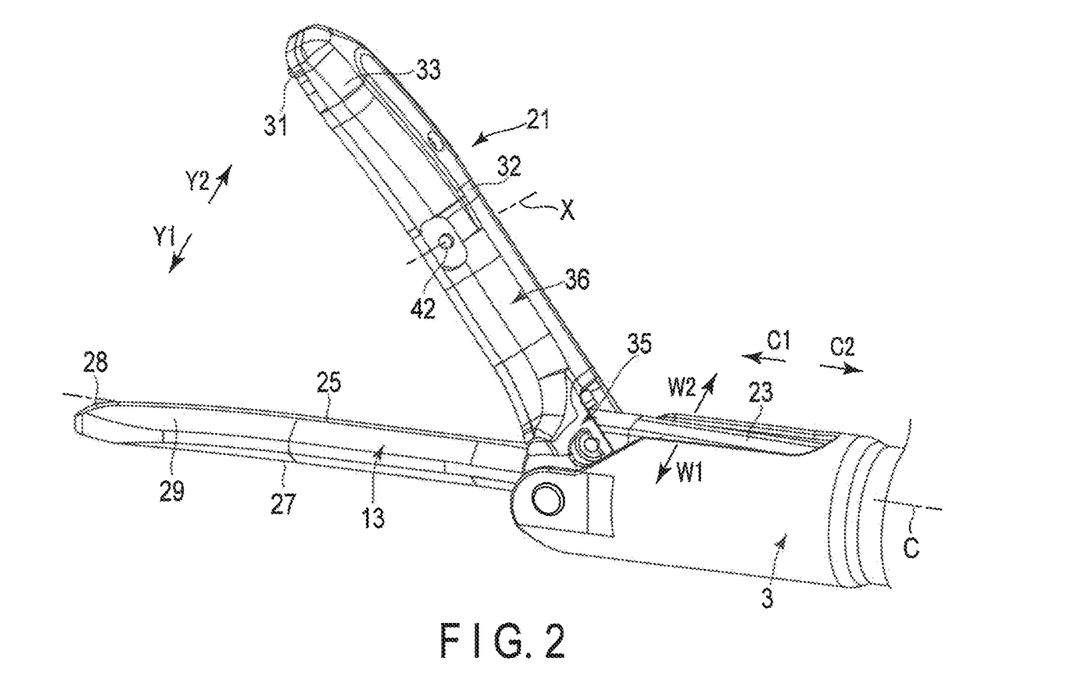
FIG. 2 is a perspective view schematically illustrating a configuration of an end effector according to the first embodiment.
Figure 3:
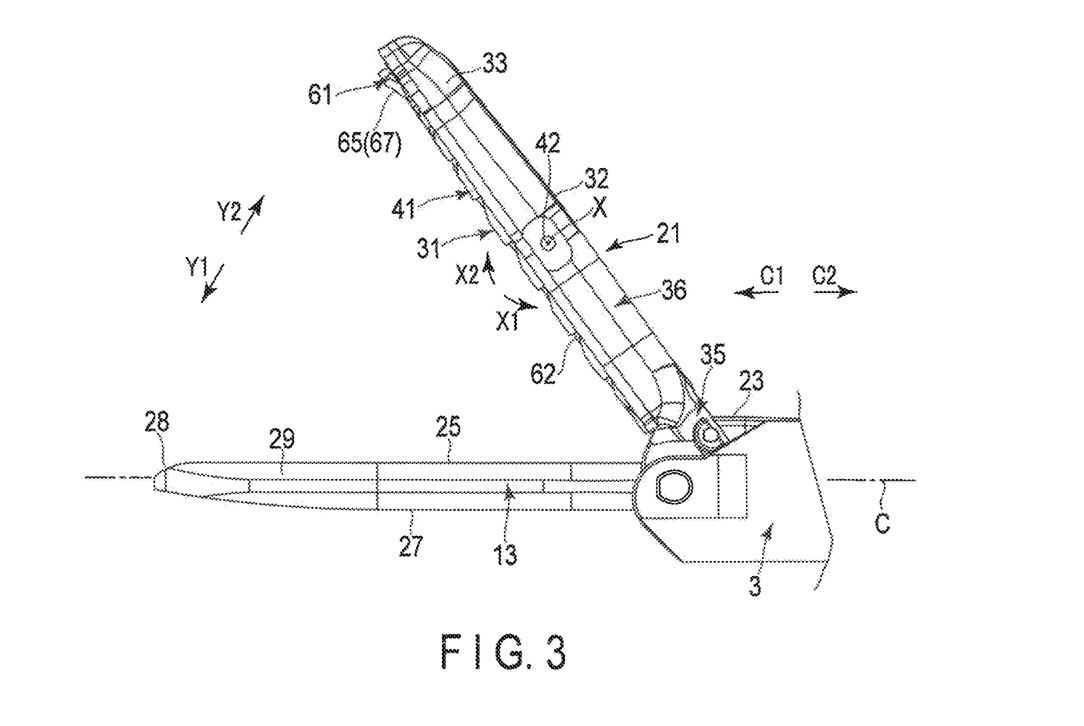
FIG. 3 is a schematic view illustrating the end effector according to the first embodiment, as viewed from one side in a width direction of the end effector.

FIG. 2 and FIG. 3 are views illustrating a configuration of the end effector 10. Here, it is assumed that a direction crossing (substantially perpendicular to) the longitudinal axis C and crossing (substantially perpendicular to) the opening direction and closing direction of the grasping piece 21 is defined as a width direction (directions indicated by arrow W1 and arrow W2) of the end effector 10. FIG. 2 is a perspective view, and FIG. 3 illustrates the end effector 10 as viewed from one side in the width direction. As illustrated in FIG. 2 and FIG. 3, the treatment section 13 includes a treatment surface (treatment section facing surface) 25 which faces the grasping piece 21, and a back surface (treatment section back surface) 27 which faces a side opposite to the treatment surface 25. A distal portion of the treatment surface 25 is provided with a treatment section inclined surface (incline surface) 28 which inclines with respect to the longitudinal axis C. The treatment section inclined surface (rod-side inclined surface) 28 inclines in a state that the treatment section inclined surface extends toward the back surface 27 side of the treatment section 13 as extending toward the distal side. In the present embodiment, the treatment section inclined surface 28 forms a distal end of the treatment surface 25 of the treatment section 13, and extends from the distal end of the treatment surface 25 toward the proximal side. In addition, in this embodiment, a distal portion of the treatment section 13 is provided with a bending extension (rod bending portion) 29 which extends in a state of bending with respect to the longitudinal axis C in the width direction of the end effector 10.

Figure 4:
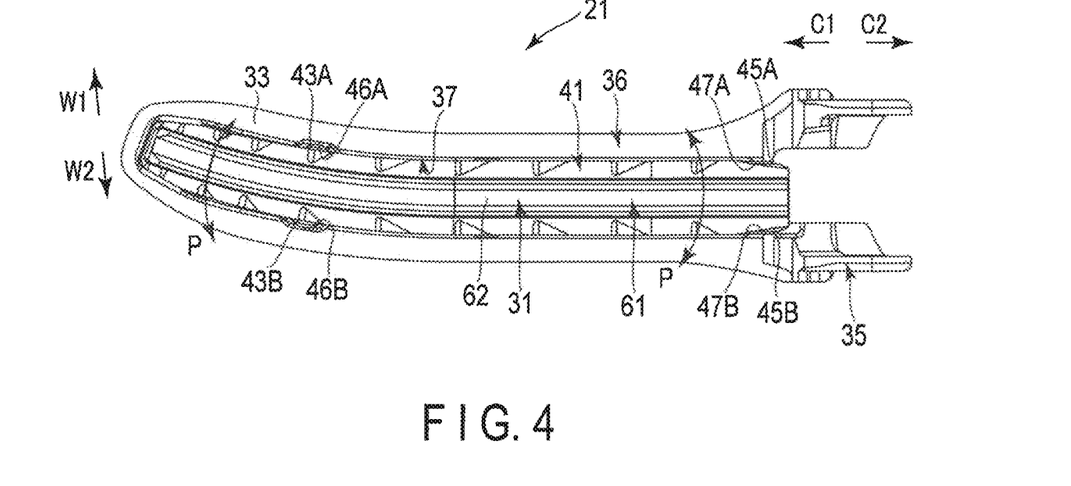
FIG. 4 is a schematic view illustrating a grasping piece according to the first embodiment, as viewed from a side toward which the grasping piece is closed.

FIG. 4 is a view illustrating the configuration of the grasping piece 21, as viewed from the side (i.e. from the arrow Y1 side) toward which the grasping piece 21 is closed. As illustrated in FIG. 2 to FIG. 4, the grasping piece 21 includes a grasping surface (grasping piece facing surface) 31 which faces the treatment section 13, and a back surface (grasping piece back surface) 32 which faces a side opposite to the grasping surface 31. In the grasping piece 21, the grasping surface 31 faces the side toward which the grasping piece 21 is closed, and the back surface 32 faces the side (arrow Y2 side) toward which the grasping piece 21 is opened. In addition, a distal portion of the grasping piece 21 is provided with a bending extension (grasping piece bending portion) 33 which extends in a state of bending with respect to the longitudinal direction of the grasping piece 21 (longitudinal axis C) in the width direction of the end effector 10. The bending extension 33 of the grasping piece 21 bends in the width direction in such a state that the bending extension 33 faces the bending extension 29 of the treatment section 13.

The grasping piece 21 includes a jaw (support member) 35 which is formed of, for example, a metal. The jaw 35 is rotatably attached to the shaft 3, and a distal portion of the movable member 23 is connected to the jaw 35. The jaw 35 extends from a proximal portion to a distal portion in the grasping piece 21. In the present embodiment, the jaw 35 is provided as one piece with a resin-made cover 36. The jaw 35 and cover 36 are integrally formed, for example, by insert molding. The cover 36 is put in close contact with a most part of an outer surface of the jaw 35. Thus, on the back surface 32, etc. of the grasping piece 21, the most part of the outer surface of the jaw 35 is not exposed to the outside of the grasping piece 21, and a most part of the back surface 32 of the grasping piece 21 is formed by the cover 36. Incidentally, in one example, the cover 36 and jaw 35 may be configured as separate members, and the cover 36 may be attached to the outer surface of the jaw 35. In another example, a resin coating may be applied to the outer surface of the jaw 35, instead of putting the cover 36 in close contact with the outer surface of the jaw 35. Here, the materials of the cover 36 and the coating are not limited to resins, and may be ceramics, rubber, or the like.

Figure 5:
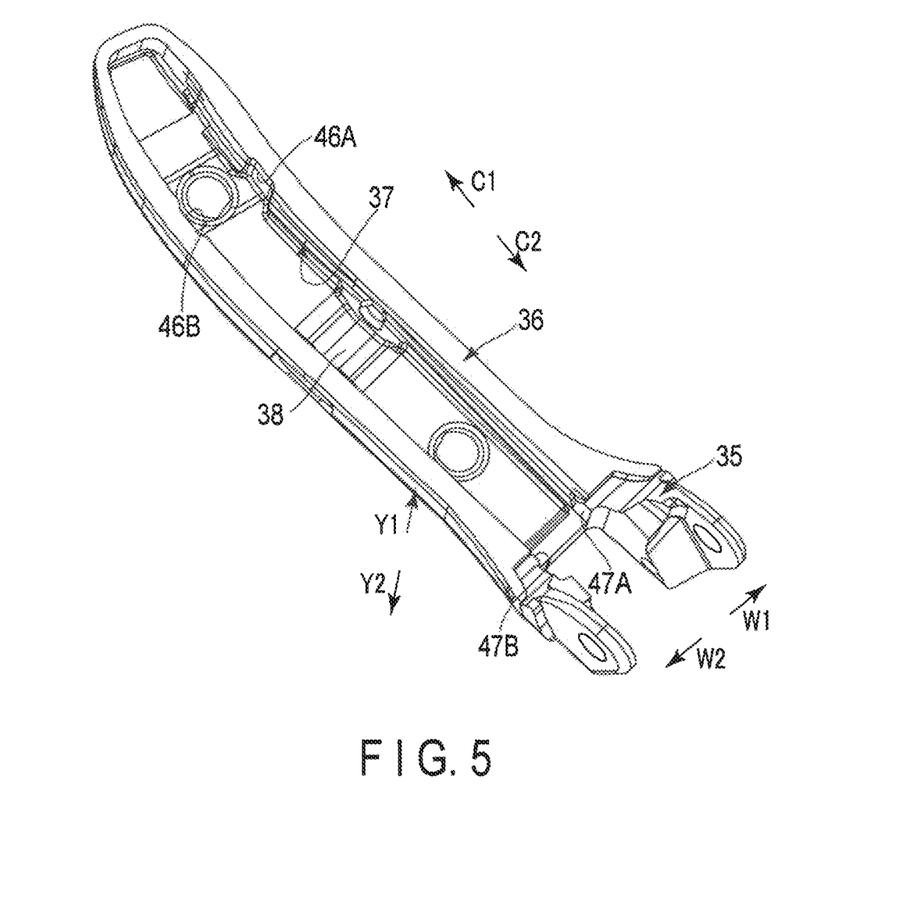
FIG. 5 is a perspective view schematically illustrating configurations of a jaw and a cover according to the first embodiment.

FIG. 5 is a perspective view illustrating the configurations of the jaw 35 and cover 36. As illustrated in FIG. 4 and FIG. 5, a recess portion (recess) 37, which is recessed toward the opening side of the grasping piece 21, is formed in the jaw 35. The recess portion 37 includes a recess bottom surface 38, and extends from the proximal portion to the distal portion of the grasping piece 21. In addition, a central position of the grasping piece 21 in the width direction of the end effector 10 is successively located in the recess portion 37 from the distal end of the recess portion 37 to the proximal end of the recess portion 37. A distal portion of the jaw 35 and a distal portion of the cover 36 form the bending extension 33 of the grasping piece 21. Thus, the distal portion of the jaw 35 and the distal portion of the cover 36 extend in a state of bending with respect to the longitudinal direction of the grasping piece 21 in the width direction of the end effector 10. In addition, a distal portion of the recess portion 37 also extends in a state of bending with respect to the longitudinal direction of the grasping piece 21 (longitudinal axis C) in the width direction of the end effector 10.

A holder member (holder) 41 is attached to the jaw 35 via a support pin 42 illustrated in FIG. 2 and FIG. 3. The holder member 41 is formed of, for example, a metal, and extends from the proximal portion to the distal portion in the grasping piece 21. In addition, the holder member 41 forms a part of the grasping surface 31. Further, a distal portion of the holder member 41 forms the bending extension 33 of the grasping piece 21. Thus, the distal portion of the holder member 41 extends in a state of bending with respect to the longitudinal direction of the grasping piece 21 in the width direction of the end effector 10. Besides, the holder member 41 is attached to the jaw 35 in a state in which the holder member 41 is inserted in the recess portion 37.

Figure 6:
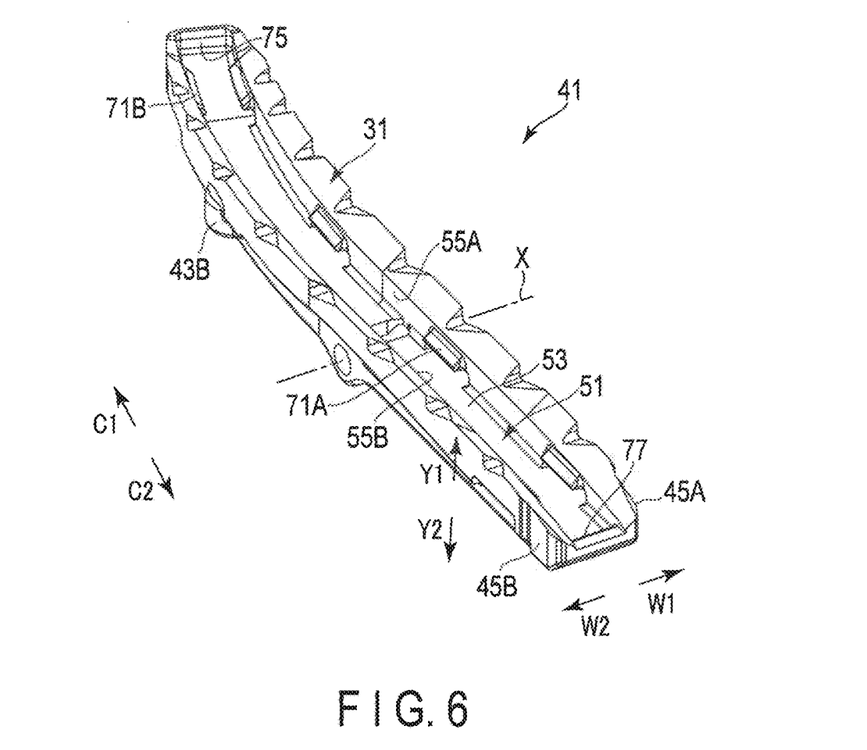
FIG. 6 is a perspective view schematically illustrating a configuration of a holder member according to the first embodiment.
Figure 7:
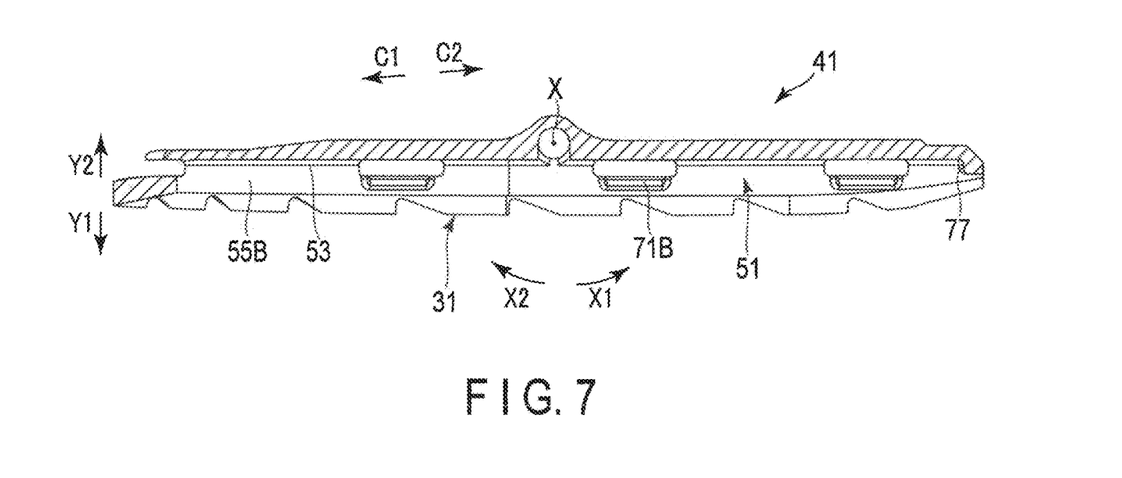
FIG. 7 is a cross-sectional view schematically illustrating the holder member according to the first embodiment by a cross section substantially perpendicular to the width direction of the end effector.
Figure 8:
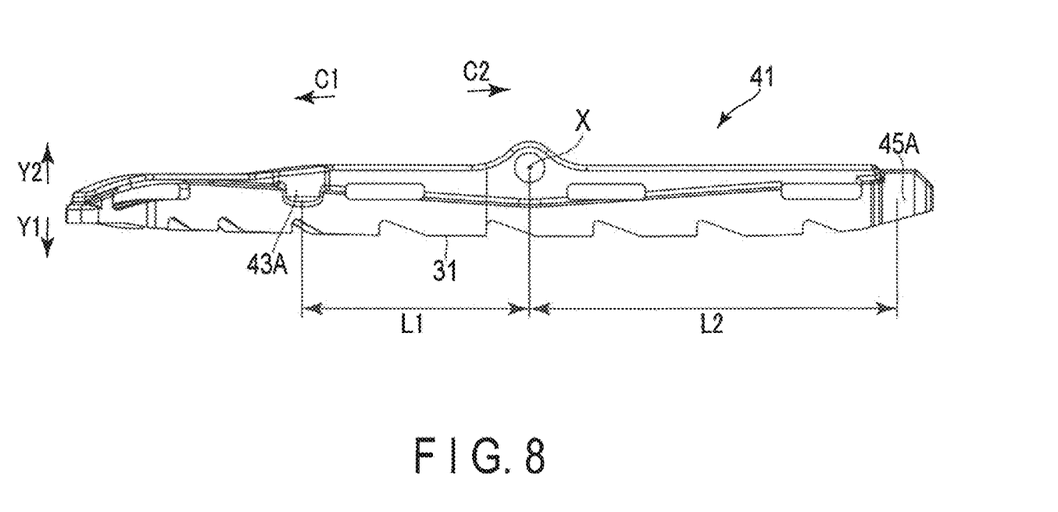
FIG. 8 is a schematic view illustrating the holder member according to the first embodiment, as viewed from one side in the width direction of the end effector.

FIG. 6 to FIG. 8 are views illustrating the configuration of the holder member 41. Here, FIG. 6 is a perspective view, and FIG. 7 illustrates the holder 41 by a cross section substantially perpendicular to the width direction of the end effector 10. In addition, FIG. 8 illustrates the holder member 41, as viewed from one side in the width direction of the end effector 10. As illustrated in FIG. 4 to FIG. 8, the holder member 41 is swingable around the support pin 42, relative to the jaw 35 and cover 36. The support pin 42 extends in the width direction of the end effector 10. Thus, the holder member 41 swings, relative to the jaw 35, around a swing axis X which extends along the width direction of the end effector 10. In addition, the support pin 42 is located in a middle portion of the grasping piece 21 in the longitudinal direction of the grasping piece 21 (the direction along the longitudinal axis C).

In a neutral position in which the holder member 41 extends substantially parallel to the jaw 35, the holder member 41 has a gap between the holder member 41 and the recess bottom surface 38 of the recess portion 37, and is not in contact with the recess bottom surface 38. In addition, the holder member 41 swings from the neutral position toward one side (arrow X1 side) in swing directions, and thereby the holder member 41 moves closer to the treatment section 13 in a part of the holder member 41 located on the distal side with respect to the support pin 42. Further, in the part located on the proximal side with respect to the support pin 42, the holder member 41 abuts on the recess bottom surface 38, and thereby the swing of the holder member 41 toward the one side in the swing directions is restricted. In addition, the holder member 41 swings from the neutral position toward the other side (arrow X2 side) in the swing directions, and thereby the holder member 41 moves closer to the treatment section 13 in a part of the holder member 41 located on the proximal side with respect to the support pin 42. Further, in the part on the distal side with respect to the support pin 42, the holder member 41 abuts on the recess bottom surface 38, and thereby the swing of the holder member 41 toward the other side in the swing directions is restricted.

A pad member (pad) 61 is attached to the holder member 41. The pad member 61 swings together with the holder member 41 around the swing axis X, relative to the jaw 35. The pad member 61 is formed of a resin material such as PTFE (polytetrafluoroethylene) and has elasticity. The pad member 61 is formed of a material which minimizes wear due to friction between the pad member 61 and the treatment section 13 of the rod member 6 and which has heat resistance. In addition, it is preferable that the pad member 61 has electrical insulation properties.

Figure 9:
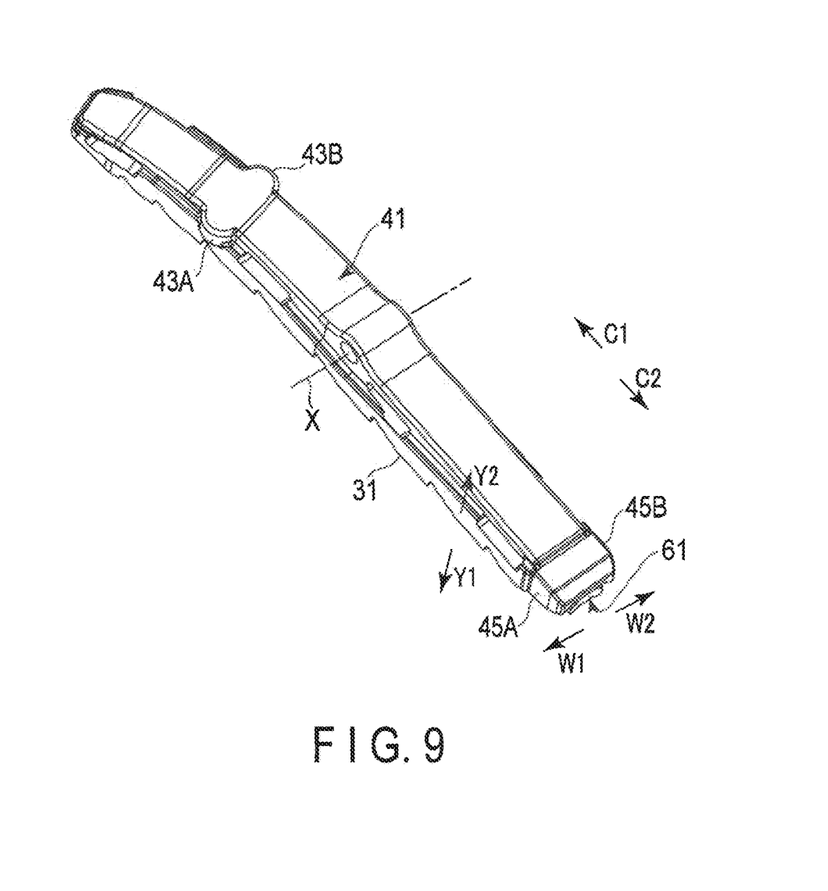
FIG. 9 is a perspective view schematically illustrating the holder member and a pad member according to the first embodiment.
Figure 10:
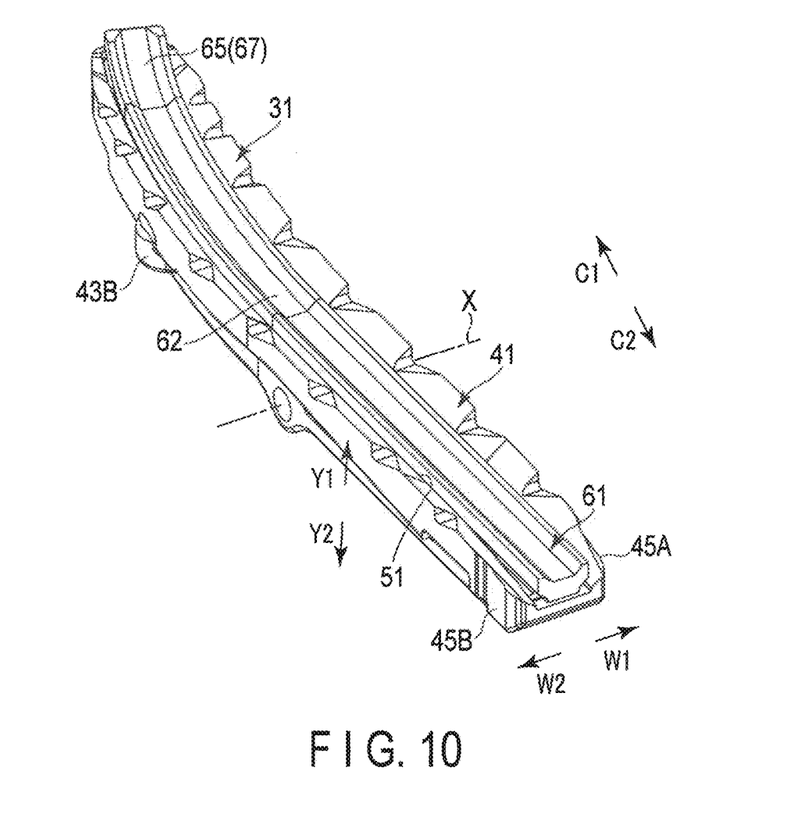
FIG. 10 is a perspective view schematically illustrating the holder member and the pad member according to the first embodiment, as viewed in a different direction from in FIG. 9.
Figure 11:
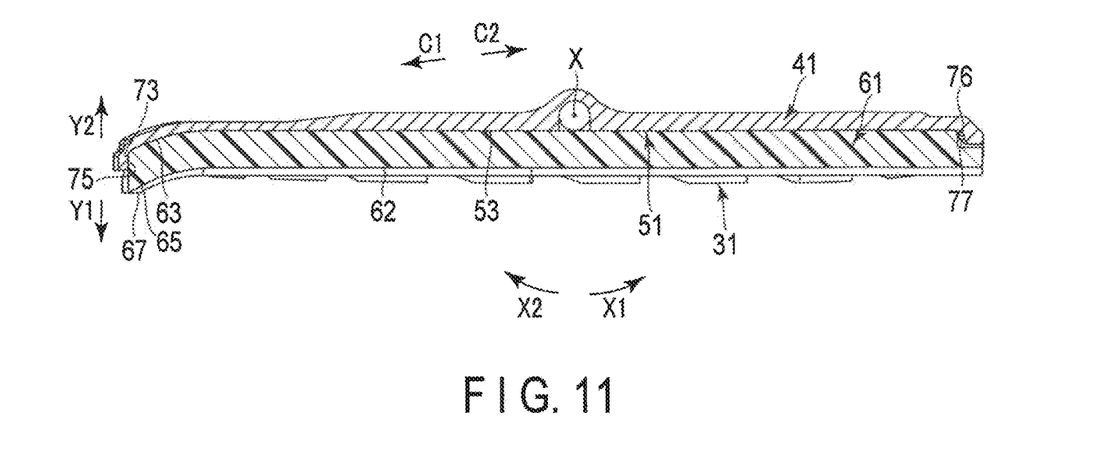
FIG. 11 is a cross-sectional view schematically illustrating the holder member and the pad member according to the first embodiment by a cross section substantially perpendicular to the width direction of the end effector.
Figure 12:
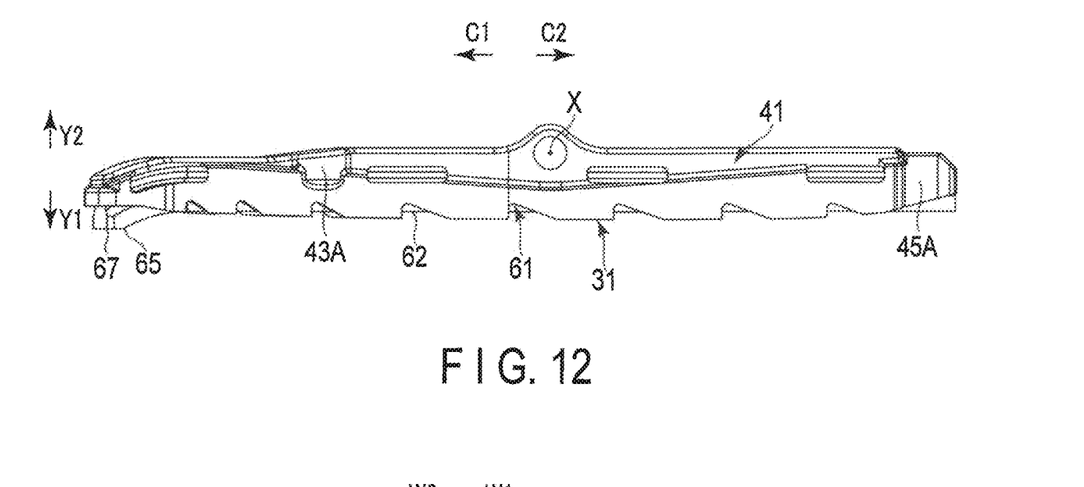
FIG. 12 is a schematic view illustrating the holder member and the pad member according to the first embodiment, as viewed from one side in the width direction of the end effector.
Figure 13:
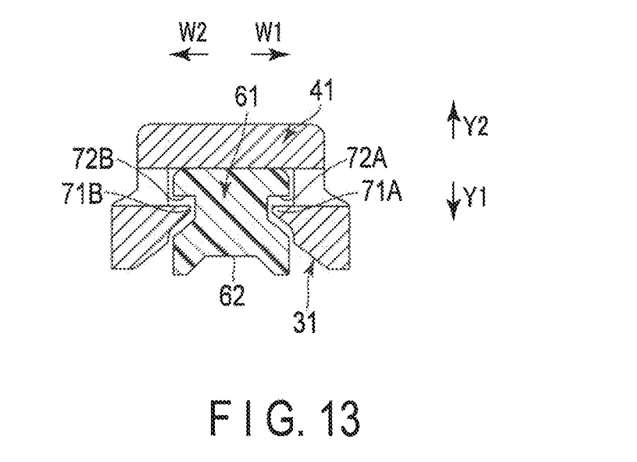
FIG. 13 is a cross-sectional view schematically illustrating the holder member and the pad member according to the first embodiment by a cross section substantially perpendicular to a longitudinal direction of the grasping piece.

FIG. 9 to FIG. 13 are views illustrating the holder member 41, and the pad member 61 which is attached to the holder member 41. Here, FIG. 9 is a perspective view, and FIG. 10 is a perspective view taken in a different direction from in FIG. 9. In addition, FIG. 11 illustrates the holder member 41 and pad member 61 by a cross section substantially perpendicular to the width direction of the end effector 10. FIG. 12 illustrates the holder member 41 and pad member 61, as viewed from one side in the width direction of the end effector 10. Besides, FIG. 13 illustrates the holder member 41 and pad member 61 by a cross section substantially perpendicular to the longitudinal direction of the grasping piece 21 (the extending direction of the pad member 61).

As illustrated in FIG. 4, FIG. 6, FIG. 8, FIG. 9 and FIG. 12, the holder member 41 includes abutment portions 43A and 45A which face one side (arrow W1 side) in the width direction of the end effector 10, and abutment portions 43B and 45B which face the other side (arrow W2 side) in the width direction of the end effector 10. The abutment portions (abutment surface) 43A and 43B are located on the distal side with respect to the support pin 42 and swing axis X, and are located at substantially mutually identical positions in the direction along the longitudinal axis C. In addition, a separation distance L1 from the support pin 42 toward the distal side up to the abutment portion 43A, 43B is large. Furthermore, the abutment portions (abutment surface) 45A and 45B are located on the proximal side with respect to the support pin 42 and swing axis X, and are located at substantially mutually identical positions in the direction along the longitudinal axis C. In addition, a separation distance L2 from the support pin 42 toward the proximal side up to the abutment portion 45A, 45B is large.

As illustrated in FIG. 4 and FIG. 5, the recess portion 37 of the jaw 35 is provided with a receiving portion 46A on which the abutment portion 43A abuts, and a receiving portion 46B on which the abutment portion 43B abuts. By the abutment portions 43A and 43B and receiving portion (receiving surface) 46A and 46B, in the abutment portion 43A and 43B having the large separation distance L1 from the support pin 42 toward the distal side, the movement of the holder member 41 relative to the jaw 35 in the width direction of the end effector 10 is restricted. In addition, the recess portion 37 of the jaw 35 is provided with a receiving portion 47A on which the abutment portion 45A abuts, and a receiving portion 47B on which the abutment portion 45B abuts. By the abutment portions 45A and 45B and receiving portions (receiving surface) 47A and 47B, in the abutment portions 45A and 45B having the large separation distance L2 from the support pin 42 toward the proximal side, the movement of the holder member 41 relative to the jaw 35 in the width direction of the end effector 10 is restricted. Besides, in the holder member 41, in the parts other than the abutment portions 43A, 43B, 45A and 45B, a gap is provided between the holder member 41 and jaw 35 in the width direction of the end effector 10.

As described above, in the present embodiment, the movement of the holder member 41 relative to the jaw 35 in the width direction of the end effector 10 is restricted in the abutment portion 43A and 43B having the large separation distance L1 from the support pin 42 toward the distal side, and in the abutment portions 45A and 45B having the large separation distance L2 from the support pin 42 toward the proximal side. Thus, the rotation of the holder member 41 relative to the jaw 35 around an axis substantially parallel to the opening direction and closing direction of the grasping piece 21, i.e. the motion indicated by arrow P, is effectively prevented. Thereby, looseness between the holder member 41 and jaw 35 is effectively suppressed in the rotational direction around the axis, which is substantially parallel to the opening direction and closing direction of the grasping piece 21.

As illustrated in FIG. 6, FIG. 7, FIG. 10, FIG. 11 and FIG. 13, the holder member 41 includes a recess portion (recess) 51 which is recessed toward the opening side of the grasping piece 21. The recess portion 51 extends from the proximal portion to the distal portion of the grasping piece 21. The recess portion 51 includes a recess bottom surface 53 and recess side surfaces 55A and 55B. The recess bottom surface (installation surface) 53 faces the side toward which the grasping piece 21 closes, i.e. toward the treatment section 13 side. In the present embodiment, since the distal portion of the holder member 41 extends in a state of bending with respect to the longitudinal direction of the grasping piece 21 in the width direction of the end effector 10, a distal portion of the recess portion 51 also extends in a state of bending with respect to the longitudinal direction of the grasping piece 21 in the width direction of the end effector 10. In addition, the central position of the grasping piece 21 in the width direction of the end effector 10 is successively located in the recess portion 51 from the distal end of the recess portion 51 to the proximal end of the recess portion 51. The pad member 61 is attached to the holder member 41 in a state in which the pad member 61 is inserted in the recess portion 51.

Figure 14:
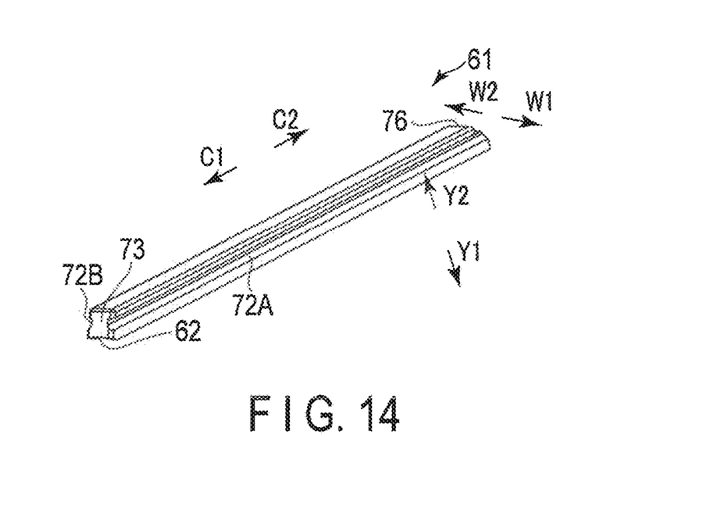
FIG. 14 is a perspective view schematically illustrating the pad member according to the first embodiment in a natural state in which the pad member is removed from the holder member.

FIG. 14 is a view illustrating the pad member 61 in a natural state in which the pad member 61 is removed from the holder member 41. As illustrated in FIG. 14, in the natural state in which the pad member 61 is removed from the holder member 41, the pad member 61 extends straight, i.e. in a straight-line shape. In the grasping piece 21, the pad member 61 is attached to the holder member 41 in the state in which the pad member 61 is elastically deformed from the natural state. In the present embodiment, since the distal portion of the recess portion 51 extends in a state of bending with respect to the longitudinal direction of the grasping piece 21 in the width direction of the end effector 10, the pad member 61 elastically deforms along the shape of the recess portion 61 from the natural state by the attachment of the pad member 61 to the holder member 41. Thereby, a distal portion of the pad member 61 also extends in a state of bending with respect to the longitudinal direction of the grasping piece 21 (longitudinal axis C) in the width direction of the end effector 10.

As illustrated in FIG. 2 to FIG. 14, the pad member 61 extends from the proximal portion to distal portion in the grasping piece 21. In addition, the pad member 61 forms a part of the grasping surface 31 of the grasping piece 21. The pad member 61 includes an abutment surface 62 which can abut on the treatment surface 25 of the treatment section 13 by the grasping piece 21 closing relative to the treatment section 13. The abutment surface 62 becomes a part of the grasping surface 31. In the state in which the abutment surface 62 abuts on the treatment surface 25, the holder member 41 has a gap between the holder member 41 and the treatment surface 25 of the treatment section 13. Accordingly, even in the state in which the abutment surface 62 abuts on the treatment surface 25, the part excluding the abutment surface 62 in the grasping surface 31 does not come in contact with the treatment surface 25.

The pad member 61 is disposed along the recess bottom surface (installation surface) 53 of the recess portion 51 of the holder member 41. Specifically, the pad member 61 extends over the recess bottom surface 53 from the proximal side toward the distal side. A distal portion of the recess bottom surface 53 is provided with a holder inclined surface 63 which inclines with respect to the longitudinal direction of the grasping piece 21. The holder inclined surface 63 inclines in a state that the holder inclined surface 63 extends toward the side toward which the grasping piece 21 is closed as extending toward the distal side. Specifically, the holder inclined surface 63 extends toward the treatment section 13 side as extending toward the distal side. In the present embodiment, the holder inclined surface 63 forms a distal end of the recess bottom surface 53 of the holder member 41, and extends from the distal end of the recess bottom surface 53 toward the proximal side.

Since the holder member 41 is provided with the holder inclined surface 63, the pad member 61 elastically deforms from the natural state by the pad member 61 being attached to the holder member 41. Thereby, in the distal portion of the abutment surface 62 of the pad member 61, a pad inclined surface 65, which inclines with respect to the longitudinal direction of the grasping piece 21, is formed due to the inclination of the holder inclined surface 63. The pad inclined surface 65 inclines in a state that the pad inclined surface 65 extends toward the side toward which the grasping piece 21 is closed as extending toward the distal side. Specifically, the pad inclined surface 65 extends toward the treatment section 13 side as extending toward the distal side. In the present embodiment, the pad inclined surface 65 forms a distal end of the abutment surface 62 of the pad member 61, and extends from the distal end of the abutment surface 62 toward the proximal side.

The treatment section inclined surface 28 faces the pad inclined surface 65. In addition, in the state in which the abutment surface 62 of the pad member 61 abuts on the treatment surface 25 of the treatment section 13, the pad inclined surface 65 abuts on the treatment section inclined surface 28. It is preferable that the pad inclined surface 65 is substantially parallel to the holder inclined surface 63. It is also preferable that in the state in which the pad member 61 abuts on the treatment section 13, the pad inclined surface 65 becomes substantially parallel to the treatment section inclined surface 28. Besides, the pad inclined surface 65 projects toward the treatment section 13 side, compared to the part of the abutment surface 62 excluding the pad inclined surface 65. Specifically, by the pad inclined surface 65, a projection portion (projection) 67 projecting toward the side, toward which the grasping piece 21 is closed, is formed in the abutment surface 62.

The recess side surface 55A of the holder member 41 is provided with a holder engaging portion 71A, and the recess side surface 55B is provided with a holder engaging portion 71B. Each of the holder engaging portions (holder engagement) 71A and 71B projects inward in the width direction of the end effector 10, and extends from the proximal side toward the distal side. Each of the holder engaging portions 71A and 71B is provided from the proximal portion to distal portion of the grasping piece 21. In the present embodiment, each of the holder engaging portions 71A and 71B extends intermittently in the extending direction of the holder member 41, and is divided into four extension ranges in the extending direction of the holder member 41. In addition, the holder engaging portions 71A and 71B extend in substantially mutually identical ranges in the longitudinal direction of the grasping piece 21. Note that each of the holder engaging portions 71A and 71B may be divided into two or three extension ranges, or may be divided into five or more extension ranges, in the extending direction of the holder member 41. Moreover, each of the holder engaging portions 71A and 71B may continuously extend from the proximal end to distal end.

The pad member 61 is provided with pad engaging portions (pad engagement) 72A and 72B which are recessed inward in the width direction of the end effector 10. Each of the pad engaging portions 72A and 72B extends from the proximal side toward the distal side. The pad engaging portion 72A is engaged with the holder engaging portion 71A, and the pad engaging portion 72B is engaged with the holder engaging portion 71B. Even in the state in which each pad engaging portion 72A, 72B is engaged with a corresponding one of the holder engaging portions 71A and 71B, the pad member 61 is movable relative to the holder member 41 in the extending direction of the pad member 61. Note that each of the pad engaging portions 72A and 72B may extend over the entire length, or over a partial range, in the extending direction of the pad member 61 (the longitudinal direction of the grasping piece 21). However, even when each of the pad engaging portions 72A and 72B extends over the partial range in the extending direction of the pad member 61, each of the pad engaging portions 72A and 72B extends over a large part of the range in the extending direction of the pad member 61, for example, over a range of 80% or more of the entire length in the extending direction of the pad member 61. Thus, each of the pad engaging portions 72A and 72B extends from the proximal portion to distal portion of the grasping piece 21. In addition, in this embodiment, the cross section of the pad member 61 perpendicular to the extending direction of the pad member 61 has a substantially uniform shape from the proximal side toward the distal side over the range in which the pad engaging portions 72A and 72B extend.

The pad member 61 can abut on the holder engaging portion 71A from the side opposite to the treatment section 13 side, i.e. from the side toward which the grasping piece 21 opens. Similarly, the pad member 61 can abut on the holder engaging portion 71B from the side opposite to the treatment section 13 side. By the pad member 61 abutting on the holder engaging portion 71A or 71B from the side opposite to the treatment section 13 side, the movement of the pad member 61 relative to the holder member 41 toward the treatment section 13 side can be restricted. Specifically, the holder engaging portion 71A, 71B forms a restriction portion (third regulator) which restricts the movement of the pad member 61 relative to the holder member 41 toward the side toward which the grasping piece 21 closes.

In the present embodiment, the holder engaging portion 71A, 71B has a projecting shape, and the pad engaging portion 72A, 72B has a recess shape, but this is not restrictive. In one example, each of the holder engaging portions 71A and 71B may be recessed outward in the width direction of the end effector 10, and each of the pad engaging portions 72A and 72B may project outward in the width direction of the end effector 10. In this case, each of the holder engaging portions 71A and 71B extends continuously from the proximal portion to distal portion of the grasping piece 21 (recess portion 51). In addition, each of the pad engaging portions 72A and 72B is provided from the proximal portion to distal portion of the grasping piece 21, and each of the pad engaging portions 72A and 72B may be provided continuously, or may be provided intermittently, from the proximal end to distal end. However, also in this case, it is preferable that each of the pad engaging portions 72A and 72B extends over the entire length in the extending direction of the pad member 61 (the longitudinal direction of the grasping piece 21), or extends over a large part of the range in the extending direction of the pad member 61.

In addition, a distal portion of the pad member 61 is provided with an abutment surface 73 which faces the distal side. In the present embodiment, the abutment surface 73 forms a distal end of the pad member 61. Besides, a distal portion of the recess portion 51 of the holder member 41 is provided with a receiving surface 75 which faces the proximal side. The abutment surface 73 can abut on the receiving surface 75 from the proximal side. By the abutment surface 73 abutting on the receiving surface 75 from the proximal side, the movement of the pad member 61 relative to the holder member 41 toward the distal side is restricted. Specifically, the receiving surface 75 forms a restriction portion (first regulator) which restricts the movement of the pad member 61 relative to the holder member 41 toward the distal side.

Furthermore, a proximal portion of the pad member 61 is provided with an abutment surface 76 which faces the proximal side. In this embodiment, a step is formed by the abutment surface 76. In addition, a proximal portion of the recess portion 51 of the holder member 41 is provided with a receiving surface 77 which faces the distal side. The abutment surface 76 can abut on the receiving surface 77 from the distal side. By the abutment surface 76 abutting on the receiving surface 77 from the distal side, the movement of the pad member 61 relative to the holder member 41 toward the proximal side is restricted. Specifically, the receiving surface 77 forms a restriction portion (second regulator) which restricts the movement of the pad member 61 relative to the holder member 41 toward the proximal side.

Next, the function and advantageous effects of the grasping treatment instrument 1 according to the present embodiment will be described. When the grasping piece 21 of the grasping treatment instrument 1 is formed, each of the jaw 35, cover 36, holder member 41 and pad member 61 is formed. As described above, the pad member 61 extends straight in the natural state. Thus, in the pad member 61 in the natural state, the part bending with respect to the longitudinal direction of the pad member 61, and the inclined surface, which inclines with respect to the longitudinal direction of the pad member 61, are not formed. Accordingly, the pad member 61 can easily be formed at low cost by cutting work or extrusion molding.

In addition, in the pad member 61, the cross section perpendicular to the extending direction of the pad member 61 has a substantially uniform shape from the proximal side toward the distal side over the range in which the pad engaging portions 72A and 72B extend. Further, each of the pad engaging portions 72A and 72B extends over the entire length or over a large part of the range in the extending direction of the pad member 61. Thus, in the pad member 61, the cross section perpendicular to the extending direction of the pad member 61 has a substantially uniform shape over at least the large part of the range in the extending direction of the pad member 61. Accordingly, in the manufacture of the pad member 61, the time and labor and the cost will be further decreased.

When the pad member 61 is attached to the holder member 41, the distal portion of the pad member 61 is inserted into the proximal portion of the recess portion 51 of the holder member 41. Then, each pad engaging portion 72A, 72B is engaged with a corresponding one of the holder engaging portions 71A and 71B, and the pad member 61 is moved relative to the holder member 41 toward the distal side in the recess portion 51. At this time, since the movement of the pad member 61 is guided by the holder engaging portions 71A and 71B, the pad member 61 can easily be guided toward the distal side. Further, the pad member 61 is moved toward the distal side up to the position in which the part between the abutment surface 73 and abutment surface 76 in the longitudinal direction of the pad member 61 is inserted in the recess portion 51. Thereby, the pad member 61 is attached to the holder member 41. In the above-described manner, in the present embodiment, the pad member 61 is easily attached to the holder member 41 at low cost.

Additionally, in the present embodiment, since the distal portion of the recess portion 51 extends in a state of bending with respect to the longitudinal axis C in the width direction of the end effector 10, the pad member 61 elastically deforms from the straight natural state by the attachment of the pad member 61 to the holder member 41. In addition, by the elastic deformation of the pad member 61, the distal portion of the pad member 61 bends with respect to the longitudinal direction of the grasping piece 21 (longitudinal axis C) in the width direction of the end effector 10. In the manner as described above, in this embodiment, the distal portion of the pad member 61 can easily be bent in the width direction of the end effector 10, and the bending extension (grasping piece bending portion) 33, which extends in the state of bending with respect to the longitudinal direction of the grasping piece 21 in the width direction of the end effector 10, can easily be formed at low cost in the distal portion of the grasping piece 21.

Additionally, in the present embodiment, the distal portion of the recess bottom surface (installation surface) 53 of the holder member 41 is provided with the holder inclined surface 63 which inclines in a state that the holder inclined surface 63 extends toward the treatment section 13 side as extending toward the distal side. Thus, by the pad member 61 being attached to the holder member 41, the pad member 61 elastically deforms from the natural state due to the inclination of the holder inclined surface 63. By the elastic deformation of the pad member 61 due to the inclination of the holder inclined surface 63, the pad inclined surface 65, which inclines with respect to the longitudinal direction of the grasping piece 21, is formed on the distal portion of the abutment surface 62 of the pad member 61. In the manner as described above, in the present embodiment, the pad inclined surface 65, which inclines in the state that the pad inclined surface 65 extends toward the treatment section side 13 as extending toward the distal side, is easily formed at low cost on the distal portion of the abutment surface 62 of the pad member 61. Specifically, the projection portion 67, which projects toward the closing side of the grasping piece 21 on the abutment surface 62, is easily formed in the pad member 61 at low cost.

As described above, in the present embodiment, the time and labor and the cost are reduced in the manufacture of the pad member 61, in the attachment of the pad member 61 to the holder member 41, in the formation of the bending extension 33 in the grasping piece 21, and the formation of the pad inclined surface 65 and projection portion 67 in the pad member 61. Therefore, the grasping piece 21 can easily be manufactured at low cost.

Additionally, in the state in which the pad member 61 is attached to the holder member 41, the movement of the pad member 61 relative to the holder member 41 toward the treatment section 13 side is restricted by the holder engaging portions (third regulator) 71A and 71B. Further, the movement of the pad member 61 relative to the holder member 41 toward the distal side is restricted by the receiving surface (first regulator) 75, and the movement of the pad member 61 relative to the holder member 41 toward the proximal side is restricted by the receiving surface (second regulator) 77. In the present embodiment, by the holder member 41 being provided with the holder engaging portions 71A and 71B and receiving surfaces 75 and 77, the pad member 61 is prevented from being removed from the recess portion 51 of the holder member 41. Thereby, the removal of the pad member 61 from the holder member 41 is effectively prevented.

When a treatment is performed by using the grasping treatment instrument 1, a surgeon holds the housing 2, and inserts the end effector 10 into a body cavity such as the abdominal cavity. Then, in the state in which a treatment target, such as a biological tissue, is disposed between the grasping piece 21 and treatment section 13, the handle 11 is closed relative to the grip 8, and the grasping piece 21 is closed relative to the treatment section 13. Thereby, the treatment target is grasped between the grasping piece 21 and treatment section 13. Then, the surgeon performs an operation input by the operation button 18, and electric energy is supplied from the energy control device (not shown) to the ultrasonic transducer 16. Thereby, ultrasonic vibration is generated by the ultrasonic transducer 16, and the generated ultrasonic vibration is transmitted to the treatment section 13 through the rod member 6. In the state in which the treatment target is grasped between the grasping piece 21 and treatment section 13, the ultrasonic vibration is transmitted to the treatment section 13, and thereby frictional heat occurs between the vibrating treatment section 13 and the treatment target. By the frictional heat, the grasped treatment target is cut and, at the same time, coagulated.

In the present embodiment, the distal portion of the treatment surface 25 is provided with the treatment section inclined surface 28, and the distal portion of the abutment surface 62 is provided with the pad inclined surface 65. In addition, the treatment section inclined surface 28 faces the pad inclined surface 65. Thus, the treatment target, such as a biological tissue, which is grasped between the grasping piece 21 and treatment section 13, is effectively prevented from slipping down toward the distal side. Furthermore, since the treatment section inclined surface 28 inclines in a state that the treatment section inclined surface 28 extends toward the back surface 27 side as extending toward the distal side, the diameter of the distal portion of the treatment section 13 is reduced by the treatment section inclined surface 28.

Additionally, in the present embodiment, as described above, the pad member 61 is attached to the holder member 41 without performing compression by heat, or the like. Thus, the deformation of the pad member 61 due to the heat occurring in the treatment, such as the above-described frictional heat, is effectively prevented. Therefore, even after a certain length of time has passed since the grasping piece 21 was manufactured, the pad member 61 hardly deforms from the time when the grasping piece 21 was manufactured, and the pad member 61 is kept in the usable state. In short, the durability of the pad member 61 is secured.

Additionally, in the present embodiment, the rotation of the holder member 41 relative to the jaw 35 around the axis substantially parallel to the opening direction and closing direction of the grasping piece 21, i.e. the motion indicated by arrow P, is effectively prevented. Thus, in the treatment, for example, the holder member 41 is prevented from abutting on the treatment section 13, and the part excluding the abutment surface 62 of the pad member 61 in the grasping piece 21 is effectively prevented from abutting on the treatment section 13. Since the part (e.g. holder member 14) excluding the pad member 61 is prevented from coming in contact with the vibrating treatment section 13, damage to the treatment section 13 and grasping piece 21 is effectively prevented.

Modifications

In one modification, if an operation input is performed by the operation button 18, ultrasonic vibration is transmitted to the treatment section 13, and also high-frequency electric power is supplied as electric energy to the treatment section 13 and the holder member 41 of the grasping piece 21 from the energy control device (not shown). Specifically, based on the operation input by the operation button 18, electric energy is supplied to the ultrasonic transducer 16, and electric energy, which is different from the electric energy supplied to the ultrasonic transducer 16, is supplied to the treatment section 13 and the holder member 41 of the grasping piece 21. Thereby, the treatment section 13 and the holder member 41 function as electrodes with mutually different electric potentials, and high-frequency current flows through the treatment target grasped between the treatment section 13 and the holder member 41. By the high-frequency current, the treatment target is denatured, and coagulation is promoted. As described above, the pad member 61 has electrical insulation properties. Thus, even when the treatment section 13 and pad member 61 abut on each other, the treatment section 13 and holder member 41 continue to function as electrodes with mutually different electric potentials.

In another modification, the holder member 41 and pad member 61 may be configured not to swing with respect to the jaw 35. In this case, the holder member 41 is fixed to the jaw 35, or the holder member 41 and jaw 35 are formed integral. When the holder member 41 and jaw 35 are formed as an integral member, the integral member is rotatably attached to the shaft 3, and is connected to the movable member 23. In addition, the integral member becomes an integral holder member (41) to which the pad member (61) is attached.

In the above-described embodiment, etc., the grasping treatment instrument (1) includes the rod member (6) which extends along the longitudinal axis (C) and which is capable of transmitting ultrasonic vibration from the proximal side to the distal side. The distal portion of the rod member (6) is provided with the treatment section (13), and the treatment section (13) includes the treatment surface (25). In addition, the grasping treatment instrument (1) includes the grasping piece (21) which is openable and closable relative to the treatment section (13), and the grasping piece (21) includes the holder member (41) and the pad member (61). The holder member (41) includes the installation surface (53) which faces the treatment section (13) side. The pad member (61) extends straight in the natural state, and is attached along the installation surface (53) of the holder member (41) in the state in which the pad member (61) is elastically deformed from the natural state. In addition, the pad member (61) includes the abutment surface (62) which is abuttable on the treatment surface (25). The distal portion of the installation surface (53) in the holder member (41) is provided with the holder inclined surface (63) which inclines in a state that the holder inclined surface extends toward the treatment section (13) side as extending toward the distal side. Further, the pad inclined surface (65), which inclines in a state that the pad inclined surface extends toward the treatment section (13) side as extending toward the distal side, is formed on the distal portion of the abutment surface (62) in the pad member (61) due to the inclination of the holder inclined surface (63).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A grasping treatment instrument comprising:
   a rod extending along a longitudinal axis, the rod being configured to transmit ultrasonic vibration from a proximal side to a distal side;
   a treatment section including a treatment surface, the treatment section being provided in a distal portion of the rod;
   a holder openable and closable relative to the treatment section, the holder including an installation surface which faces a treatment section side;
   a pad and a proximal portion of the installation surface extending straight along a longitudinal axis, the pad being attached along the installation surface of the holder, and the pad including an abutment surface configured to abut the treatment surface;
   a holder inclined surface provided on a distal portion of the installation surface in the holder, the holder inclined surface inclining in a state that the holder inclined surface extends downward toward the treatment section side as extending toward the distal side; and
   a pad inclined surface formed on a distal portion in the pad attached to the holder, the pad inclined surface being formed in a state in which the pad inclined surface is elastically deformed along an inclination of the holder inclined surface, and the pad inclined surface inclining in a state that the pad inclined surface extends toward the treatment section side as extending toward the distal side.

2. The grasping treatment instrument of claim 1, wherein the treatment section includes a back surface which faces a side opposite to the treatment surface, and
   the treatment surface includes a rod-side inclined surface which is provided on a distal portion of the treatment surface, the rod-side inclined surface inclining in a state that the rod-side inclined surface extends toward a back surface side as extending toward the distal side.

3. The grasping treatment instrument of claim 2, wherein in a state in which the abutment surface of the pad abuts on the treatment surface of the treatment section, the pad inclined surface abuts on the rod-side inclined surface.

4. The grasping treatment instrument of claim 1, wherein the holder includes a holder engagement extending from the proximal side toward the distal side, and
   the pad includes a pad engagement extending from the proximal side toward the distal side, the pad engagement being configured to be engaged with the holder engagement.

5. The grasping treatment instrument of claim 4, wherein a cross section of the pad perpendicular to an extending direction of the pad has a uniform shape from the proximal side toward the distal side in a range in which the pad engagement extends.

6. The grasping treatment instrument of claim 4, wherein the holder engagement is configured to restrict movement of the pad relative to the holder toward the treatment section side.

7. The grasping treatment instrument of claim 1, wherein the pad includes a distal abutment surface which faces the distal side in a distal portion of the pad, and a proximal abutment surface which faces the proximal side in a proximal portion of the pad, and
   the holder includes:
   a first regulator including a distal receiving surface which faces the proximal side in a distal portion of the installation surface, the first regulator being configured such that the distal abutment surface is abuttable on the distal receiving surface; and
   a second regulator including a proximal receiving surface which faces the distal side in a proximal portion of the installation surface, the second regulator being configured such that the proximal abutment surface is abuttable on the proximal receiving surface.

8. The grasping treatment instrument of claim 1, wherein the holder is swingable.

9. The grasping treatment instrument of claim 8, further comprising:
   a jaw configured to swingably support the holder.

10. The grasping treatment instrument of claim 1, wherein in a state in which the abutment surface of the pad abuts on the treatment surface of the treatment section, the holder has a gap between the holder and the treatment surface of the treatment section.

11. The grasping treatment instrument of claim 1, wherein the pad is formed of a resin material.

* * * * *